(12) United States Patent
Soma et al.

(10) Patent No.: US 8,962,323 B2
(45) Date of Patent: Feb. 24, 2015

(54) METHOD OF ISOLATING DERMAL STEM CELLS

(75) Inventors: Tsutomu Soma, Kanagawa (JP); Haruyo Yamanishi, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/496,061

(22) PCT Filed: Sep. 15, 2010

(86) PCT No.: PCT/JP2010/065981
§ 371 (c)(1),
(2), (4) Date: Mar. 14, 2012

(87) PCT Pub. No.: WO2011/034106
PCT Pub. Date: Mar. 24, 2011

(65) Prior Publication Data
US 2012/0208269 A1    Aug. 16, 2012

(30) Foreign Application Priority Data

Sep. 15, 2009   (JP) ................................. 2009-213291

(51) Int. Cl.
| | | |
|---|---|---|
| C12N 5/02 | (2006.01) | |
| C12N 5/00 | (2006.01) | |
| C12N 5/0775 | (2010.01) | |
| G01N 33/50 | (2006.01) | |

(52) U.S. Cl.
CPC .......... *C12N 5/0668* (2013.01); *G01N 33/5073* (2013.01)
USPC ............ 435/383; 435/325; 435/381; 435/375

(58) Field of Classification Search
None
See application file for complete search history.

(56) References Cited

U.S. PATENT DOCUMENTS

2007/0053884 A1   3/2007  Suda et al.

FOREIGN PATENT DOCUMENTS

WO   WO 2004/101775 A1   11/2004

OTHER PUBLICATIONS

Legg et al., Development, 2003; 130 (24) 6049-6063.*
Trempus et al., J. Investig. Dermatol., 2003: 120(4)501-511.*
Li et al., Proc. Nat'l. Acad. Sci., 1998, 95(7)3902-3907.*
Soma et al., "Shinpi no Okeru kan'yokei Kansaibo no Kyokuzai to Tokusei ni Kansuru Kaiseki," Regenerative Medicine, Feb. 5, 2010, 9(special extra issue)238, O-37-3.
Yamanishi et al., "Shinpi Kan'yokei Kansaibo no Tokusei Oyobi Kyokuzai Imaging ni Kansuru Kento," The Japanese Journal of Dermatology, Mar. 10, 2010, 120(3,special extra issue):655, p. 2-2.
Biernaskie et al., "Isolation of skin-derived precursors (SKPs) and differentiation and enrichment of their Schwann cell progeny," Nature Protocols, Jan. 1, 2006, 1(6):2803-2812.
Schlabe et al., "Isolation and culture of different epidermal and dermal cell types from human scalp suitable for the development of a therapeutical cell spray," Burns, Mar. 14, 2008, 34(3):376-384.
Shi et al., "Differentiation of dermis-derived multipotent cells into insulin-producing pancreatic cells in vitro," World J. Gastroenterol., Jan. 1, 2004, 10(17):2550-2552.
Toma et al., "Isolation of multipotent adult stem cells from the dermis of mammalian skin," Nature Cell Biology, Sep. 1, 2001, 3:778-784.
Paquet-Fifield et al., "A role for pericytes as microenvironmental regulators of human skin tissue regeneration", Journal of Clinical Investigation, Sep. 2009, pp. 2795-2806, vol. 119, No. 9.

* cited by examiner

*Primary Examiner* — Doug Schultz
(74) *Attorney, Agent, or Firm* — Foley & Lardner LLP (57) ABSTRACT

The invention provides a method of isolating dermal stem cells, having the steps of subjecting cells separated from the skin by enzyme treatment to suspension culture, and isolating cells positive for stem cell markers from the cultured cells.

4 Claims, 6 Drawing Sheets

OSTEOCYTE DIFFERENTIATION

ADIPOCYTE DIFFERENTIATION

US 8,962,323 B2

METHOD OF ISOLATING DERMAL STEM CELLS

CROSS-REFERENCE TO RELATED APPLICATIONS

This application is a National Stage application of PCT/JP2010/065981, filed Sep. 15, 2010, which claims priority from Japanese application JP2009-213291, filed Sep. 15, 2009.

FIELD OF THE INVENTION

The present invention relates to a method of isolating dermal stem cells from skin tissue.

BACKGROUND OF THE INVENTION

Stem cells are cells having both properties of multipotent potential of producing cells that are differentiated into a plurality of cells, and self-replicating potential of producing identical cells by cell division. Stem cells derived from an embryo, an early developmental stage of a fertilized egg, are embryonic stem cells (ES cells). Human ES cells are expected to be applied to regenerative medicine, but due to ethical concerns associated with the use of fertilized eggs, the creation of new ES cells is not permitted.

In recent years, as cells having properties similar to embryonic stem cells, attention has also been focused on artificially induced pluripotent stem cells (iPS cells). However, the creation of iPS cells is associated with various problems such as cancerous changes in cells and poor efficiency of generating the cells. On the other hand, somatic stem cells having capable of differentiating into a specific tissue have no such ethical problems, unlike embryonic stem cells, since they are derived from a patient's own tissue, such as bone marrow.

It is well known that, in the skin, there are epidermal stem cells in the epidermal basal layer (Non-patent document 1) and it is reported that there are follicular epithelial stem cells (Non-patent document 2) and cutaneous melanocyte stem cells (Non-patent document 3) in a region referred to as the hair follicle bulge area. On the other hand, in the dermis, thin spindle-shaped fibroblasts are present in the fiber component comprising collagen as the main ingredient, but it has not been demonstrated whether stem cells are present in the dermal fibroblasts. It is also known that in the dermis there are skin-derived precursor cells (SKP) that differentiate into a plurality of cell lineages such as adipocytes, glia cells, chondrocytes and myocytes (Non-patent document 4), but no relationship has been confirmed between dermal fibroblasts and SKP.

Mesenchymal stem cells isolated from bone marrow as precursor cells of fibroblasts (Non-patent document 5) can differentiate into various cells (osteocytes, myocytes, chondrocytes, adipocytes, etc.) belonging to the mesenchymal system, and thus are expected to be applied to regenerative medicine, such as reconstruction of bones, blood vessels and muscles. Recently, evidence is growing showing the likelihood that mesenchymal stem cells may occur in many tissues having mesenchymal tissue, and mesenchymal stem cells have also been isolated from fat, cord blood, placenta, etc. (Non-patent documents 6 to 8). However, the presence of mesenchymal stem cells in the dermis has not been shown yet.

PRIOR ART DOCUMENTS

Non-Patent Documents

[Non-patent document 1] Watt F M, J Dermato Sci. 28:173-180, 2002

[Non-patent document 2] Cotsarelis G et al., Cell. 57:201-209, 1989

[Non-patent document 3] Nishimura E K et al., Nature. 416:854-860, 2002

[Non-patent document 4] Wong C E al., J Cell Biol. 175:1005-1015, 2006

[Non-patent document 5] Pittenger M F et al., Science. 284:143-147, 1999

[Non-patent document 6] Park K W et al., Cell Metab. 8:454-457, 2008

[Non-patent document 7] Flynn A, et al., Cytotherapy. 9:717-726, 2007

[Non-patent document 8] Igura K et al., Cytotherapy. 6:543-553, 2004

SUMMARY OF THE INVENTION

Problems to be Solved by the Invention

There are very few Mesenchymal stem cells in bone marrow, and cord blood and placenta are derived from a very limited number of subjects, and therefore they are limited as the source for autologous mesenchymal stem cells. If mesenchymal stem cells can be isolated from dermis, the skin may provide a very important source of mesenchymal stem cells for use in regenerative medicine and cosmetic medicine. Thus, it is an object of the present invention to provide a method of isolating mesenchymal stem cells from the dermis.

After an investigation to demonstrate the presence of mesenchymal stem cells in the dermis as well as to establish a method for efficiently isolating mesenchymal stem cells, the present inventor has actually confirmed the presence of cells positive for stem cell markers in the perivascular area of (human) dermis. However, when a skin tissue is enzyme-treated for the purpose of isolating the cells, the expression of specific stem cell markers may markedly decrease. In the suspension culture of the enzyme-treated cells, the present inventor has found that not only the expression of markers for the stem cells is restored but the cells maintain a high differentiation ability compared to adhesion-cultured cells, and therefore has completed the present invention.

Thus, the present invention encompasses the following inventions:

(1) A method of isolating dermal stem cells comprising:
subjecting cells separated from the skin by enzyme treatment to suspension culture; and
isolating cells positive for stem cell markers from the cultured cells.

(2) The method according to (1) wherein the cells positive for stem cell markers are the CD34-positive cells.

(3) The method according to (2) wherein the CD34-positive cells are further NG2-positive.

(4) The method according to any of (1) to (3) wherein the suspension culture is carried out for a period of time sufficient to restore the expression of stem cell markers on the cells.

Effects of the Invention

Not wishing to be bound by theory, it is believed that dermal stem cells occur in the microvasculature area as a pericyte-like cell population and that they become activated at the time of skin injury, and differentiate into fibroblasts and myofibroblasts thereby to contribute to skin regeneration and restoration. Also, it is expected that the stem cells are consumed due to aging and skin stimulation, which results in not only the reduction of skin function but the reduction of the skin regenerating ability and instability of the blood vessels, thereby causing aging of skin.

In accordance with the method of the present invention, dermal stem cells can be easily isolated. The dermal stem cells obtained by the present invention are expected to contribute to elucidation of the mechanism of skin homeostasis and aging and to be used in regenerative medicine.

MODE FOR CARRYING OUT THE INVENTION

The present invention provides a method of isolating dermal stem cells comprising:
subjecting cells separated from the skin by enzyme treatment to suspension culture; and
isolating cells positive for stem cell markers from the cultured cells.

The above skin-derived cells can, but are not limited to, separation according to a method of isolating mesenchymal stem cells from the bone marrow. For example, with enzyme-treating skin tissue, the dermal cells are separated from the skin tissue. The enzyme-treatment can be carried out using a common proteolytic enzyme such as trypsin and collagenase. The skin tissue to be used may be, but not limited to, those derived from a mammal, preferably a human.

In cells that received such an enzyme treatment, the expression of a specific stem cell marker may decrease. As used herein the term "a stem cell marker" means a marker useful for isolating dermal stem cells, the expression of which decreases by the enzyme treatment for separating the cells from a tissue, such as a cell surface antigen CD34. Though the cell surface antigen CD34 known as a hematopoietic stem cell marker has been confirmed by the present inventor to be expressed at the blood vessel areas in the dermis, as described below, the amount expressed of CD34 in the cells immediately after enzyme treatment enormously decreases. Thus, even if the skin-derived cells obtained by the enzyme treatment was subjected to flow cytometry, stem cell marker-positive cells could not be sufficiently separated. Also the expression of a stem cell marker on the enzyme-treated cells may markedly decrease even when the cells are subjected to an adhesion culture which is a common culturing method of mesenchymal stem cells. However, it was found that when the cells obtained by the enzyme treatment of a skin tissue were subjected to an suspension culture for a certain period of time, the expression of a stem cell marker could be restored. Further surprisingly, dermal stem cells isolated through a suspension culture exhibit a higher differentiation ability than those obtained through an adhesion culture.

The above suspension culture may be carried out for a period of time sufficient to restore the reduced expression of a stem cell marker, e.g., for 4 hours, and if necessary, for a few days such as for 5 days. From the viewpoint of post-translational modification of a stem cell marker with a sugar chain etc., the suspension culture may preferably be carried out for 6 hours. For the suspension culture, a medium for use in culturing mesenchymal stem cells may be used. If serum is contained in the culture medium used, its adhesion to the surface of the culturing container may arise due to an adhesion factor in the serum, and thus the use of a serum-free medium may be preferred. In order to prevent the adhesion of cells with each other, methyl cellulose may be added to the culture medium. The culture medium may be used in a container for suspension culture.

Stem cell marker-positive cells can be isolated using a flow cytometer such as a cell sorter. As the cell sorter, for example MACS™ (beads system can be used. The term "stem cell marker-positive cells" means the cells that express a factor widely known as a common marker for the somatic stem cells, such as CD34, CD44, CD105, CD133, CD146, c-kit, p75NTR, integrin α6 and integrin β1. As an example of the stem cell marker-positive cells for use in the present invention, there can be mentioned CD34-positive cells. Also, by using NG2 which is a pericyte marker occurring in the perimeter of the vascular endothelial cells, dermal stem cells can be more precisely isolated. Thus, the stem cell marker-positive cells isolated in the present invention may preferably be CD34/NG2-double positive cells.

The stem cell marker-positive cells isolated may be subjected to plate culture in a culture medium for mesenchymal stem cells. By selecting and culturing highly adhesive cells among the cells, dermal stem cells that will grow into colonies can be obtained. The dermal stem cells thus obtained can differentiate into various cells such as osteocytes and adipocytes.

EXAMPLES

Next, the present invention will be explained in further details with reference to Examples. It should be noted that the present invention is not limited to them.
Experimental Method
Separation of Cells from the Human Skin Tissue After removing the blubber section with a scalpel under a stereoscopic microscope from a human skin tissue in a DMEM medium (Invitrogen) supplemented with 10% fetal bovine serum, the skin tissue was minced with scissors for autopsy to small tissue sections of 1-2 mm$^2$. Then, the tissue sections obtained were dispersed in 10 ml of a DMEM medium containing 0.1% trypsin and 0.2% collagenase in a 50 ml tube, and the skin tissue was enzymatically digested using a shaking incubator at 37° C. for 3 hours. At the end of the enzymatic digestion, 30 ml of the DMEM medium was added, and the cells were dispersed by pipetting. After centrifugation, the cells were resuspended in the DMEM medium and counted as the human tissue-derived cells.

Primary Culture of Human Tissue-Derived Cells

After the skin-derived cells separated from the human skin were suspended in 5 ml of MesenPro medium (Invitrogen), a culture medium for mesenchymal stem cells, they were plated in a non-coated T-25 culture flask (Falcon) and cultured overnight in a $CO_2$ incubator. Then the culture liquid was aspirated off leaving only the adhered cells, and 5 ml of a fresh MesenPro medium was added thereto to continue culturing. While changing the medium every three days, culturing was continued, and when the cell density reached confluence, the cells were collected, and the cells obtained were used as the human dermis-derived cells.

Sorting of Human Dermis-Derived Cells using Magnetic Beads

After the human tissue-derived cells were suspended in 10 ml of a suspension culture medium (DMEM/F-12 (3:1) (Invitrogen), 40 ng/ml FGF 2 (Sigma), 20 ng/ml EGF (R & D Systems), B27 (Invitrogen), an antimicrobial agent (Wako Pure Chemical Industries, Ltd.)), they were plated in a non-coated T-25 culture flask (Falcon) and cultured in suspension in a $CO_2$ incubator for 5 days. Then the cells were sorted out using the CD34 MicroBead Kit (Miltenyi Biotec). The operational condition was as described in a protocol provided by Miltenyi Biotec.

First, the cell mass of the suspension-cultured human skin-derived cells were physically dispersed using a Pasteur pipet with a rounded tip, and then the cell suspension was passed through a strainer (Falcon) with a hole size of 40 µm. Next, after washing once with an ice-cold MACS buffer (PBS containing 0.5% BSA and 2 mM EDTA, pH 7.2), the cells were counted, and one million cells were resuspended in 300 µl of the MACS buffer. Subsequently, 100 µl of the FcR blocking reagent was added and mixed, to which 100 µl of the CD34 microbeads was further added and mixed well again, and incubated in a refrigerator for 30 minutes. After washing with 5 ml of the MACS buffer, the cells were recovered by centrifugation, and then resuspended in 500 µl of the MACS buffer. A MS column was inserted into the magnetic field of the MACS separator and washed with 500 µl of the MACS buffer, and then the above cell suspension was applied to the column. The column was washed for three times with 500 µl of the MACS buffer, and the cells recovered thereon were used as the CD34-negative skin-derived cells. Then the column was removed from the magnetic field and placed on a tube for recovery. One ml of the MACS buffer was added to the column, extruded from the top of the column using an attached plunger, and the cells recovered were used as the CD34-positive skin-derived cells. The respective CD34-positive or -negative skin-derived cells were cultured in the MesePro medium, and the cells obtained were used as the human CD34-positive dermis-derived cells or the human CD34-negative dermis-derived cells.

Colony-Forming Assay

After the dermis-derived cells were suspended in the MesenPro medium, they were plated in a 6 cm or 10 cm petri dish at a low concentration, and cultured in a $CO_2$ incubator for 2 weeks. After the culturing was complete, they were stained with Giemsa stain to count the colonies formed. Giemsa stain was carried out as follows. The cells were fixed in methanol and slightly air-dried. Then a Giemsa stain (Nacalai Tesque Inc.) diluted five-fold with tap water was poured onto the petri dish to stain, and finally washed with running tap water for an appropriate period of time.

Subculture of Human Dermis-Derived Cells

The subculture of human dermis-derived cells was carried out using the MesenPro medium by plating at a ratio of 1000 cells per $cm^2$. Culturing was continued while changing the medium for every three days, and when the cell density reached confluence, the cells were stored frozen and subcultured.

Differentiation Culture Experiment

For the human dermis-derived cells derived from each sample that was subcultured in the MesenPro medium, culturing for differentiation into the adipocytes, osteocytes, and chondrocytes was carried out using the Human Mesenchymal Stem Cell Functional Identification Kit of R & D Systems. The respective dermis-derived cells were suspended in the αMEM medium supplemented with 10% fetal bovine serum, and 40,000 cells in the case of adipocyte differentiation and 18,000 cells in the case of osteocyte differentiation were plated into a two-hole chamber slide coated with an acid collagen solution (Koken). Then, culturing was continued while replacing the culture medium with the αMEM medium supplemented with 10% fetal bovine serum for every three days.

Then, in the case of adipocyte differentiation, when the cells reached confluence, the medium was replaced with a 10% fetal bovine serum-containing αMEM medium to which an additive for adipocyte differentiation contained in the above kit had been added, and cultured for two weeks. Also, in the case of osteocyte differentiation, when the cells reached subconfluence, the medium was replaced with a 10% fetal bovine serum-containing αMEM medium to which an additive for osteocyte differentiation contained in the above kit had been added, and cultured for two weeks. For differentiation to chondrocytes, 250,000 dermis-derived cells were centrifuged in a 15 ml tube, and after washing with 1 ml of DMEM/F-12 (Invitrogen), the medium was replaced with 0.5 ml of DMEM/F-12 medium to which an additive for chondrocyte differentiation contained in the above kit had been added, and the cells were cultured for three weeks as they were in the form of a mass.

Oil Red O Staining

The dermis-derived cells that were subjected to a fat differentiation culture were fixed in a 4% paraformaldehyde-phosphate buffer at room temperature for 15 minutes. After rinsing in sterile distilled water, it was treated with 60% isopropanol at room temperature for 1 minute, and then reacted with the oil red O stain at room temperature for 15 minutes. It was treated in 60% isopropanol for differential staining, and after being acclimated to sterile distilled water, it was microscopically examined.

Kossa Staining

The dermis-derived cells that were subjected to a bone differentiation culture were fixed in a 4% paraformaldehyde-phosphate buffer at room temperature for 15 minutes. After rinsing in sterile distilled water for three times, a 5% aqueous solution of silver nitrate prepared immediately before use was added. The chamber slide was allowed to stand still at about 10 cm apart from the bottom of a 27 W fluorescent lamp, the whole was covered with an aluminum foil, and reacted at room temperature for one hour and half. After the reaction was complete, it was washed with sterile distilled water for three times, a 5% aqueous solution of sodium thiosulfate was added thereto and allowed to stand for 2 minutes. By further washing three times with sterile distilled water, it was microscopically examined.

Staining of the Human Skin Tissue

The human skin tissue was embedded in a frozen tissue-embedding reagent OTC compound (Sakura Finetek Japan) and sliced with a frozen section preparation instrument Cryostat (Leica) to prepare frozen sections. Frozen sections air-dried at room temperature were fixed at room temperature for 15 minutes using cold acetone cooled at −20° C. for 15 minutes. Then, after washing with TBS, they were blocked with a serum-free blocking reagent (DAKO) for 30 minutes, and were reacted at 4° C. overnight with an anti-human CD34 antibody (Becton Dickinson) and a rabbit anti-human NG2 antibody (Millipore) which had been diluted 100-fold with 3% BSA-containing TBST. After washing twice with TBST for 15 minutes and once with TBS for 15 minutes for a total of three times, they were reacted with an Alexa 488-labelled anti-rabbit IgG and a secondary antibody (Invitrogen) labelled with an Alexa 594-labelled anti-mouse IgG which had been diluted 200-fold with 3% BSA-containing TBST for 1 hour. After the sections after reaction were washed twice with TBST for 15 minutes and once with TBS for 15 minutes for a total of three times, they were subjected to nuclear staining with Hoechist 33258, and then examined using a cofocal fluorescent microscope LSM5 PASCAL (Zeiss).

Cell Staining

After washing the dermis-derived cells that were subjected to adipocyte differentiation or osteocyte differentiation with PBS, the cells were fixed in 4% PFA for 15 minutes. After washing with TBS, the cells were incubated with a 0.1% Triton X100-containing TBS solution for 15 minutes for enhancing the permeability of the cell membrane (permealization). In the case of chondrocyte differentiation, frozen sections of the cell mass of the dermis-derived cells after the differentiation experiment were prepared, and then treated in a manner similar to the above procedure and used in staining. Then, after blocking with a serum-free blocking reagent (DAKO) for 30 minutes, they were incubated at 4° C. overnight with an anti-FABP-4 antibody (for the detection of fats), an anti-osteocalcin antibody (for the detection of bone) and an anti-aggrecan antibody (for the detection of cartilage) which had been diluted 25-fold with 3% BSA-containing TBST. After washing twice with TBST for 15 minutes and once with TBS for 15 minutes for a total of three times, they were reacted with an Alexa 350 (or Alexa 448, Alexa 594)-labelled secondary antibody (Invitrogen) which had been diluted 200-fold with 3% BSA-containing TBST for 1 hour. After they were washed twice with TBST for 15 minutes and once with TBS for 15 minutes for a total of three times, they were mounted with the Vector Sheered (Vector) containing an antifading reagent and a cover glass, and then examined using a fluorescent microscope (Olympus).

Quantitative PCR

Using Isogen (Nippon Gene), total RNA was extracted from the dermis-derived cells according to the provided protocol. The concentration of the purified total RNA was determined using a nucleic acid quantitation instrument Nanodrop (Thermo Scientific). For each of the dermis-derived cells, using an equal amount of total RNA with a random primer (Invitrogen) and a reverse transcriptase Superscript III (Invitrogen), cDNA was synthesized according to the manual of Invitrogen Corporation. Using a reaction reagent LighCycler FastStart DNA Master PLUS SYBR Green (Roche) and a reaction instrument LightCycler (Roche) with the synthesized cDNA as the template, quantitative PCR was carried out. The composition condition was as described in Roches's protocol. The PCR condition comprised an initial denaturation at 95° C. for 10 minutes, denaturation at 95° C. for 10 seconds, annealing at 60° C. for 10 seconds, and an extension at 72° C. for 10 seconds. The sequences of the primers used are as follows:

G3PDH:
(SEQ ID NO: 1)
Forward primer: 5'-GCACCGTCAAGGCTGAGAAC-3'

(SEQ ID NO: 2)
Reverse primer: 5'-ATGGTGGTGAAGACGCCAGT-3'

HGF:
(SEQ ID NO: 3)
Forward primer: 5'-GAGGGAAGGTGACTCTGAATGAG-3'

(SEQ ID NO: 4)
Reverse primer: 5'-AATACCAGGACGATTTGGAATGGCAC-3'

NANOG:
(SEQ ID NO: 5)
Forward primer: 5'-TGCTTATTCAGGACAGCCCT-3'

(SEQ ID NO: 6)
Reverse primer: 5'-TCTGGTCTTCTGTTTCTTGACT-3'

SDF1a:
(SEQ ID NO: 7)
Forward primer: 5'-TGSGCTACAGATGCCCATGC-3'

(SEQ ID NO: 8)
Reverse primer: 5'-CCACTTTAGCTTCGGGTCAA-3'

Using a software attached to LightCycler, the amount expressed of each gene was determined. G3PDH was used as the internal standard, and in the quantitation of each gene this was used to correct the amount of cDNA of the control group.

Results

Figure 1:
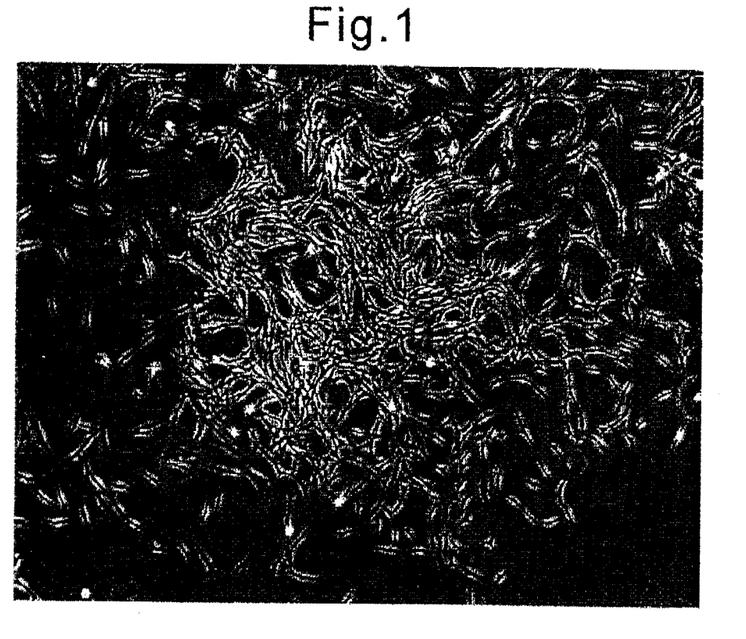
FIG. 1 shows a micrograph of fibroblast-like cells obtained by culturing highly adhesive cells among cells isolated from human dermis according to the method of the present invention in a medium for mesenchymal stem cells.
Figure 2:
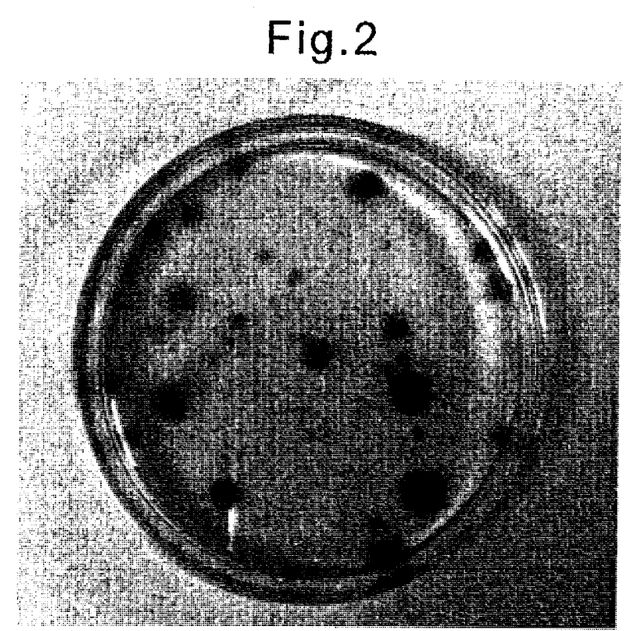
FIG. 2 shows colonies formed by the fibroblast-like cells shown in FIG. 1.
Figure 3:
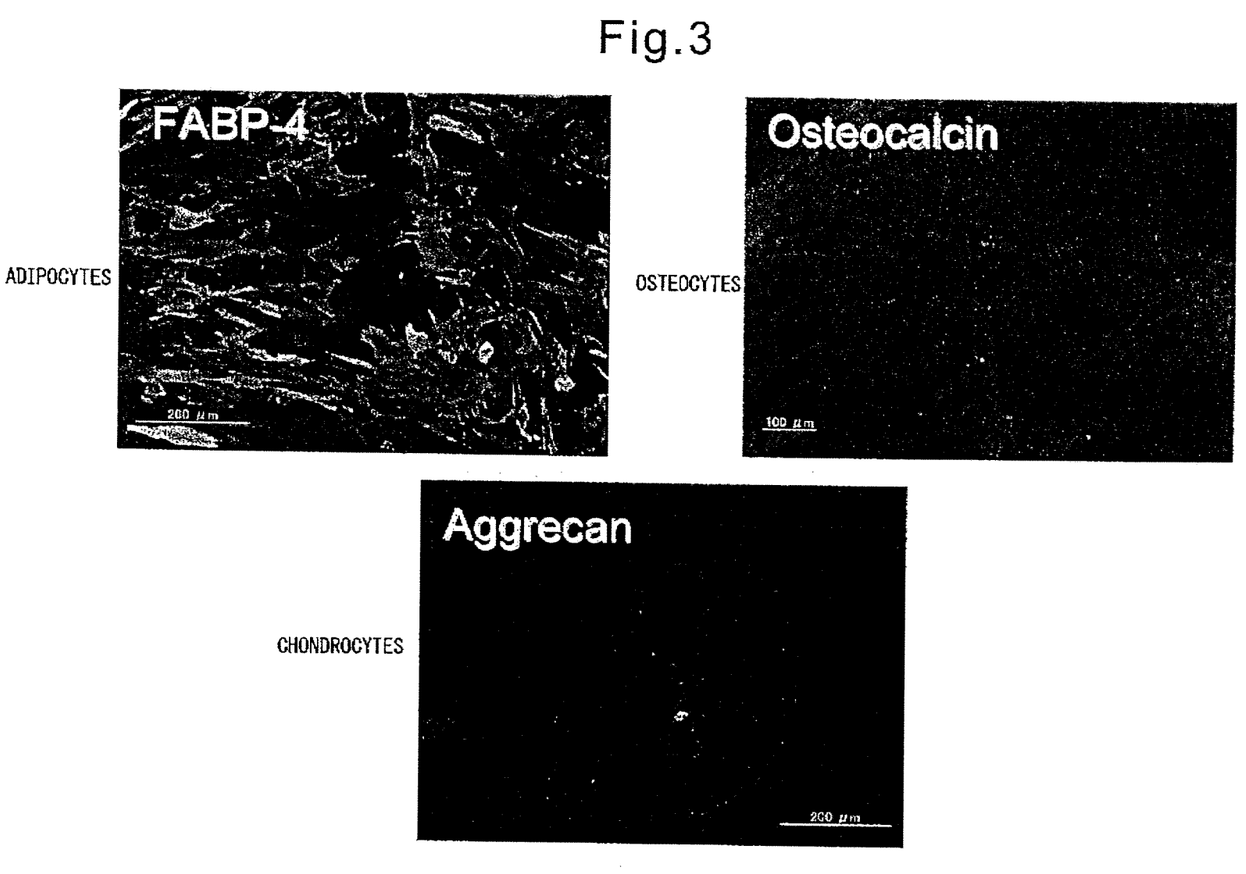
FIG. 3 shows that fibroblast-like cells may differentiate into adipocytes, osteocytes and chondrocytes.

The blubber-removed human skin tissue was separated with enzyme, and the cells adhered in 24 hours to the non-coated culture tray were cultured in MesenPro medium, a culture medium for mesenchymal stem cells. As a result, at a time point of one week after starting the culture, the appearance of fibroblast-like cells was noted as shown in FIG. 1. Then, after growing these cells to confluency, they were subjected to a colony assay, and a multitude of circular colonies were formed (FIG. 2). Also, when they were subcultured twice to examine differentiation into the cells of fat, bone and cartilage, respective differentiation markers were expressed at a time point of 2-3 weeks after starting the culture as shown in FIG. 3, confirming the differentiation into fat, bone and cartilage. The above results revealed that mesenchymal stem cells are present in the human skin.

Figure 4:
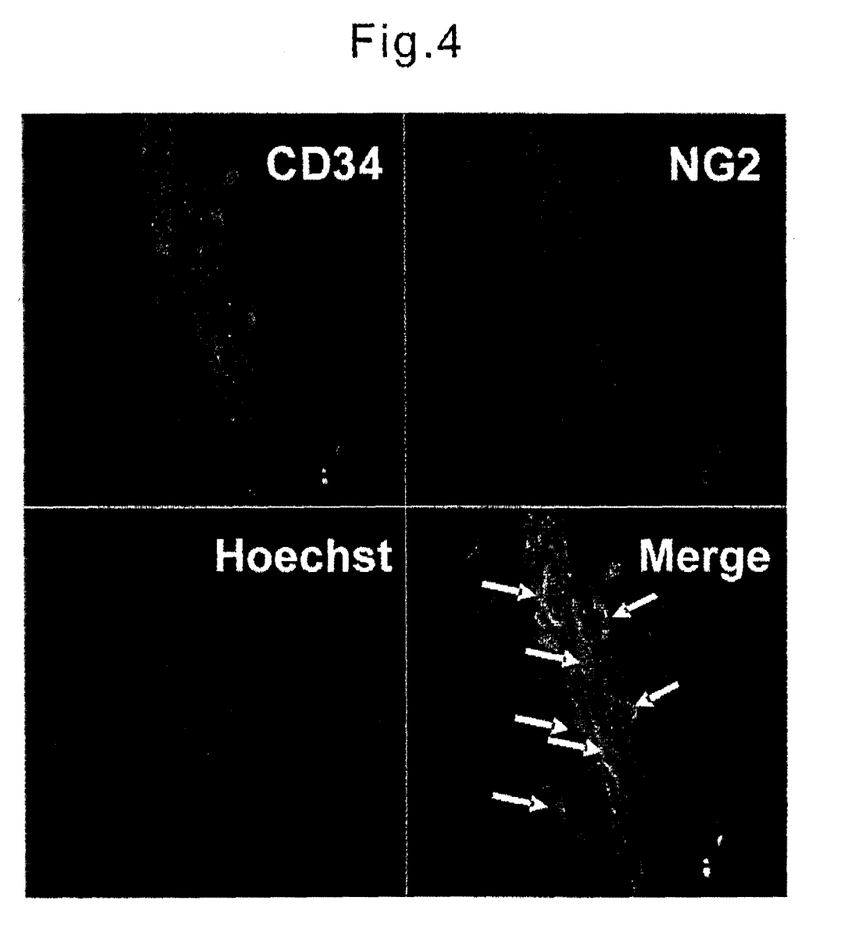
FIG. 4 represents a histochemical stain of a blood vessel area in the dermis stained using stem cell markers CD34 and NG2 as well as a nuclear staining agent Hoechst 33258.

Then, the distribution of mesenchymal stem cells in the human skin was demonstrated by histological staining. First, the distribution of CD34, which is well known as a marker for precursor cells and stem cells such as hematopoietic stem cells, vascular endothelial cells and fat-derived stem cells, in the human dermal tissue was investigated. The result indicated that CD34 was localized in the vascular area different from fibroblasts sporadically present in the dermal collagen fibers (data not shown). Then, in double staining with a pericyte marker NG2 and a stem cell marker CD34 conducted to differentiate from vascular endothelial cells, it was found that the cells that are doubly positive for the pericyte marker NG2 and the stem cell marker CD34 were present in the vascular area (FIG. 4). Thus, it was highly probable that these cell populations are dermal mesenchymal stem cells.

Figure 5:
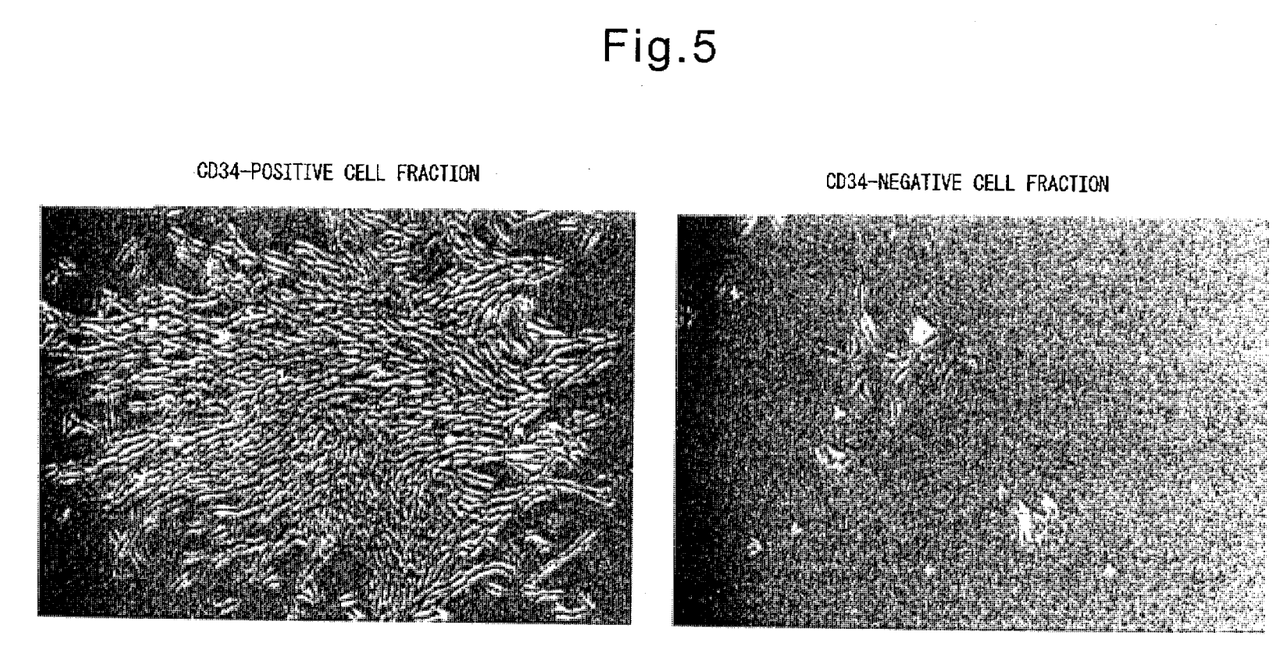
FIG. 5 represents a photomicrograph showing the colony-forming ability of a cell fraction obtained by sorting out the CD34-positive cells derived from human dermis.
Figure 6:
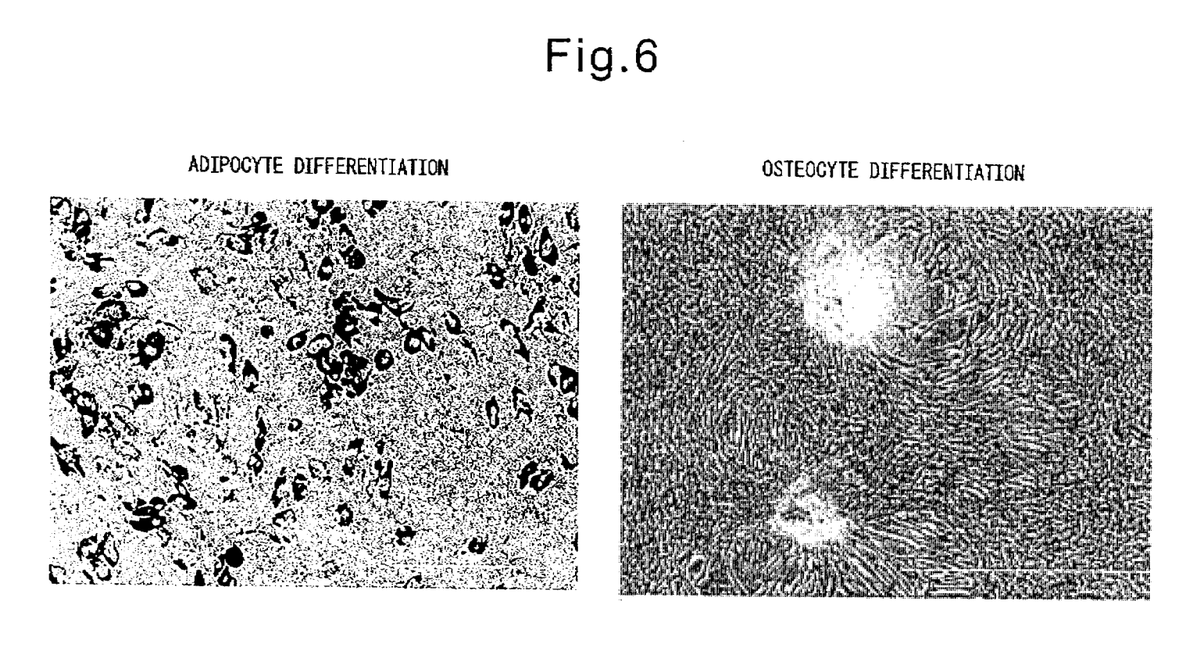
FIG. 6 represents a photomicrograph showing that CD34-positive cells derived from human dermis are the dermal mesenchymal stem cells that will differentiate into the fat and the bone.
Figure 7:
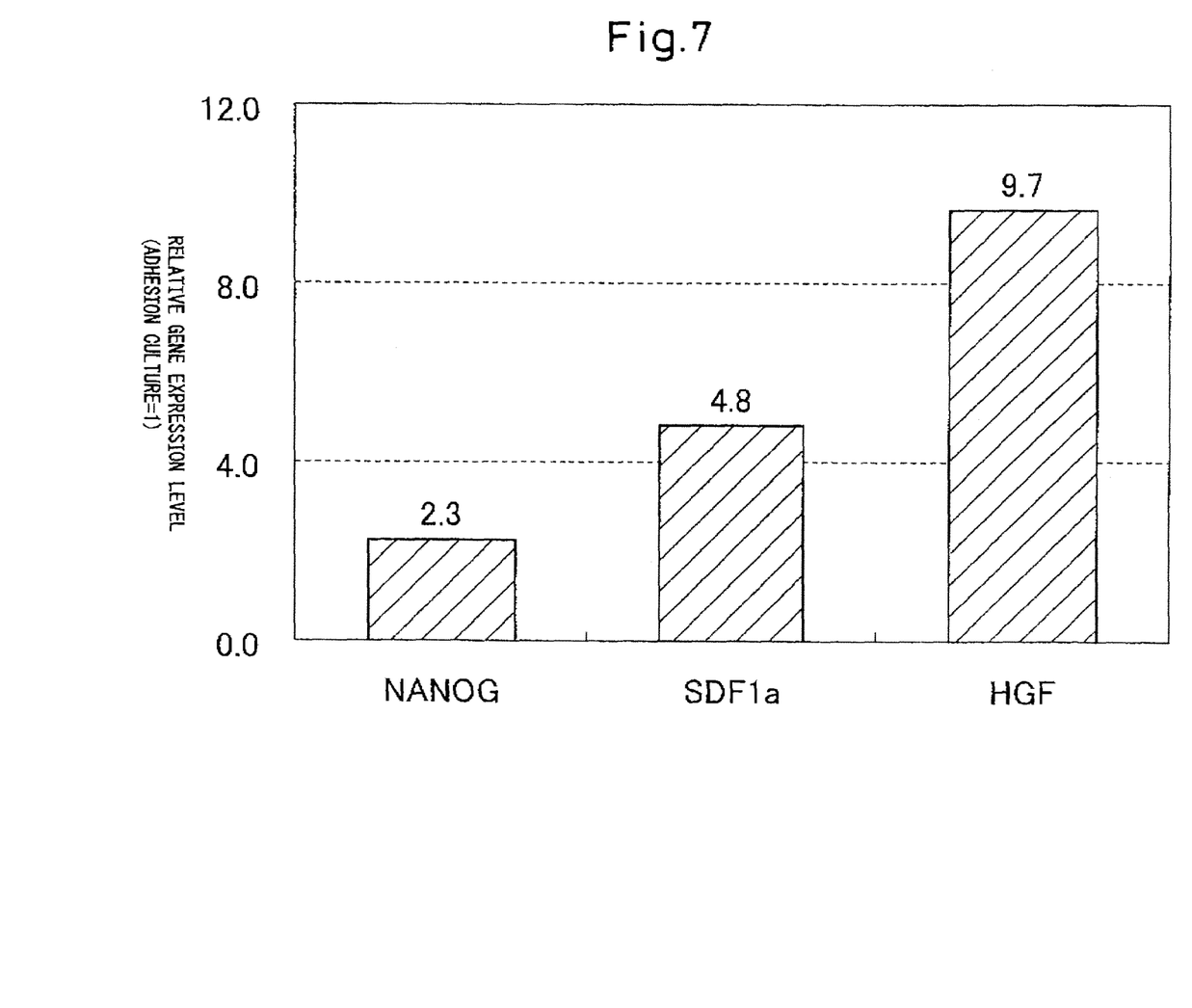
FIG. 7 represents a graph showing the ratio of gene expression of mesenchymal stem cell markers NANOG, SDF-1α and HGF in the dermal stem cells obtained according to the method of the present invention, in which the expression ratio was comparison with the amount expressed of the stem cells obtained by the adhesion culture.

In order to demonstrate that the NG2/CD34-doubly positive cells are dermal mesenchymal stem cells or that dermal mesenchymal stem cells can be efficiently isolated using these markers, the cells were subjected to cell sorting with these markers and the differentiation ability was investigated. The results with CD34 are presented. When a human skin tissue of a 2 cm$^2$ size was separated by treating in an enzyme solution (a DMEM medium containing 0.1% trypsin/0.2% collagenase) at 37° C. for 3 hours, about 100,000 cells were obtained. The cells were subjected to suspension culture for up to 5 days, and then recovered by centrifugation, and physically separated using a Pasteur pipet with the tip rounded by burning. The cells obtained (one million) were subjected to cell sorting using the CD34 MicroBead Kit (Milternyi Biotec). After the respective CD34-positive or -negative cell fractions were suspended in the MesePro medium, they were plated in a 10 cm petri dish at a ratio of 5,000 cells per dish, and cultured in a $CO_2$ incubator for two weeks. When the cells were examined under an inverted microscope at a time point of two weeks after starting the culture, the CD34-positive cell fraction formed a multitude of propagative colonies, whereas only a few differentiated colonies were noted in the CD34-negative cell fraction and subsequently the cells could not be grown, either (FIG. 5). When the cells after the separation of skin tissue were directly subjected to cell sorting without suspension culture, no colonies were noted in the CD34-positive cell fraction, either. Next, when the CD34-positive cell fraction was subcultured twice in the MesenPro medium to investigate the ability of differentiate into the fat and the bone, they differentiated into the oil red O-positive adipocytes or the Kossa-positive osteocytes (FIG. 6). The dermal mesenchymal stem cells obtained by cell sorting were found to maintain a high differentiation ability compared to the dermal mesenchymal stem cells obtained by the adhesion method (Table 1). Furthermore, in the dermal mesenchymal stem cells obtained by cell sorting, the expression of factors highly expressed in mesenchymal stem cells such as NANOG, SDF-1α and HGF was clearly higher than in the dermal mesenchymal stem cells obtained by the adhesion method (FIG. 7).

TABLE 1

Differentiation Ability of Dermal Mesenchymal Stem Cells

|  | Adipocytes | Osteocytes |
| --- | --- | --- |
| SK-MSC$_s$* | ++ | + |
| SK-MSC$_s$ (CD34+) | +++ | +++ |

*SK-MSC$_s$: dermal mesenchymal stem cells isolated after adhesion culture
SKMSC$_s$ (CD34): dermal mesenchymal stem cells isolated through CD34 magnetic bead sorting
+++: 10,000 ≤ differentiated cells,
++: 1,000 ≤ differentiated cells <10,000,
+: 100 ≤ differentiated cells <1,000,
±: 10 ≤ differentiated cells <100,
−: differentiated cells <10

[Sequence Listing]

The invention claimed is:

1. A method of isolating dermal stem cells comprising:
subjecting cells separated from the skin by enzyme treatment to suspension culture; and
isolating adhesive cells positive for stem cell markers from the cultured cells, wherein the cells are CD34/NG2-double positive.

2. The method according to claim 1, wherein the suspension culture is carried out for a period of time sufficient to restore the expression of stem cell markers on the cells.

3. The method of isolating dermal stem cells according to claim 1, wherein the stem cells are mesenchymal stem cells.

4. The method according to claim 1, wherein the suspension culture is carried out for at least 4 hours.

* * * * *

```
SEQUENCE LISTING

<160> NUMBER OF SEQ ID NOS: 8

<210> SEQ ID NO 1
<211> LENGTH: 20
<212> TYPE: DNA
<213> ORGANISM: Artificial
<220> FEATURE:
<223> OTHER INFORMATION: forward primer for G3PDH

<400> SEQUENCE: 1
gcaccgtcaa ggctgagaac                                                 20

<210> SEQ ID NO 2
<211> LENGTH: 20
<212> TYPE: DNA
<213> ORGANISM: Artificial
<220> FEATURE:
<223> OTHER INFORMATION: reverse primer for G3PDH

<400> SEQUENCE: 2
atggtggtga agacgccagt                                                 20

<210> SEQ ID NO 3
<211> LENGTH: 23
<212> TYPE: DNA
<213> ORGANISM: Artificial
<220> FEATURE:
<223> OTHER INFORMATION: forward primer for HGF

<400> SEQUENCE: 3
gagggaaggt gactctgaat gag                                             23

<210> SEQ ID NO 4
<211> LENGTH: 26
<212> TYPE: DNA
<213> ORGANISM: Artificial
<220> FEATURE:
<223> OTHER INFORMATION: reverse primer for HGF

<400> SEQUENCE: 4
aataccagga cgatttggaa tggcac                                          26
```

```
<210> SEQ ID NO 5
<211> LENGTH: 20
<212> TYPE: DNA
<213> ORGANISM: Artificial
<220> FEATURE:
<223> OTHER INFORMATION: forward primer for NANOG

<400> SEQUENCE: 5
tgcttattca ggacagccct                                               20

<210> SEQ ID NO 6
<211> LENGTH: 22
<212> TYPE: DNA
<213> ORGANISM: Artificial
<220> FEATURE:
<223> OTHER INFORMATION: reverse primer for NANOG

<400> SEQUENCE: 6
tctggtcttc tgtttcttga ct                                            22

<210> SEQ ID NO 7
<211> LENGTH: 20
<212> TYPE: DNA
<213> ORGANISM: Artificial
<220> FEATURE:
<223> OTHER INFORMATION: forwrd primer for SDF1a

<400> SEQUENCE: 7
tgsgctacag atgcccatgc                                               20

<210> SEQ ID NO 8
<211> LENGTH: 20
<212> TYPE: DNA
<213> ORGANISM: Artificial
<220> FEATURE:
<223> OTHER INFORMATION: reverse primer for SDF1a

<400> SEQUENCE: 8
ccactttagc ttcgggtcaa                                               20
```